United States Patent
Osada et al.

(10) Patent No.: US 7,094,802 B2
(45) Date of Patent: Aug. 22, 2006

(54) PKB-3564 SUBSTANCE WITH NEOVASCULARIZATION INHIBITORY ACTIVITY

(75) Inventors: Hiroyuki Osada, Niiza (JP); Hideaki Kakeya, Wako (JP); Hiroshi Konno, Akita (JP); Susumu Kanazawa, Kanagawa (JP)

(73) Assignees: Riken, Saitama (JP); Institute of Biotechnology Applied to Soil Eumycetes, Tokyo (JP)

( * ) Notice: Subject to any disclaimer, the term of this patent is extended or adjusted under 35 U.S.C. 154(b) by 0 days.

(21) Appl. No.: 10/475,804

(22) PCT Filed: Apr. 24, 2002

(86) PCT No.: PCT/JP02/04086
§ 371 (c)(1),
(2), (4) Date: Jun. 21, 2004

(87) PCT Pub. No.: WO02/088137
PCT Pub. Date: Nov. 7, 2002

(65) Prior Publication Data
US 2005/0033066 A1    Feb. 10, 2005

(30) Foreign Application Priority Data
Apr. 25, 2001 (JP) .................. 2001-127576

(51) Int. Cl.
*A61K 31/35* (2006.01)
*C07D 493/00* (2006.01)

(52) U.S. Cl. ................... 514/453; 549/330

(58) Field of Classification Search .......... 549/358, 549/330; 514/453
See application file for complete search history.

(56) References Cited

OTHER PUBLICATIONS

J. Folkman; European Journal of Cancer; vol. 32A, No. 14; pp. 2534-2539; 1996.

Craig B. Thompson; Science; vol. 267; pp. 1456-1462; Mar. 10, 1995.

Albert Zlotnik et al.; Immunity; vol. 12; pp. 121-127; Feb. 2000.

Shigekazu nagata; Cell; vol. 88; pp. 355-365; Feb. 7, 1997.

Lee, Julie C. et al.: J. Organic Chemical, 1996, vol. 61, No. 10, pp. 3232-3233.

Y. Hu et al., Organic Letters, vol. 3 (2001), No. 11, pp. 1649-1652.

H. Kakeya et al., J. Am. Chem. Soc., vol. 124 (2002), No. 14, pp. 3496-3497.

*Primary Examiner*—Joseph K. McKane
*Assistant Examiner*—Robert Shiao
(74) *Attorney, Agent, or Firm*—Birch, Stewart, Kolasch & Birch, LLP

(57) ABSTRACT

A compound represented by formula (I) wherein $R^1$ represents hydrogen atom and $R^2$ represents hydroxyl group, or $R^1$ and $R^2$ may combine together to represent oxo group or oxime group; $R^3$ represents hydrogen atom and $R^4$ represents hydroxyl group, or $R^3$ and $R^4$ may combine together to represent oxo group or oxime group; $R^5$ represents hydrogen atom and $R^6$ represents hydroxyl group, or $R^5$ and $R^6$ may combine together to represent oxo group or oxime group; $R^7$ represents hydrogen atom and $R^8$ represents hydrogen atom, or $R^7$ and $R^8$ may combine together to represent oxo group or oxime group; $R^9$ and $R^{10}$ represent hydrogen atom, an alkyl group, or an alkenyl group. The compound is useful as an active ingredient of a medicament having angiogenesis suppressive activity, apoptosis suppressive activity, and cell cycle inhibitory activity (I)

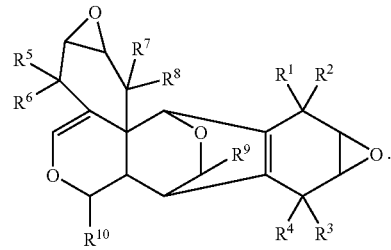

9 Claims, No Drawings

PKB-3564 SUBSTANCE WITH NEOVASCULARIZATION INHIBITORY ACTIVITY

This application is the national phase under 35 U.S.C. § 371 of PCT International Application No. PCT/JP02/04086 which has an International filing date of Apr. 24, 2002, which designated the United States of America.

TECHNICAL FIELD

The present invention relates to novel compounds which are useful as active ingredients of medicaments such as angiogenesis suppressants.

BACKGROUND ART

Apoptosis, a mode of cell death reported in the 1970s, differs from necrosis and is a cell death induced through a specific intracellular signal transduction system [Cell, 88, 355–365 (1997)]. Apoptosis is involved in pathologic conditions of variety of diseases. A control of apoptosis may possibly contribute to progresses of therapeutic treatments of these diseases. For example, a deviation from a normal apoptosis control mechanism and a resulting acceleration of cell death are believed to induce articular rheumatism, hepatitis with viral infection such as hepatitis B and C, fulminant hepatitis, diabetes, myocardial infarction, ulcerative colitis, brightism, alopecia, neurodegenerative diseases such as Alzheimer's disease and Parkinson's disease, ischemic brain damage, acquired immune deficiency syndrome, ecstatic cardiomyopathy and the like [Science, 267, 1456–1462 (1995)].

Examples of physiological stimulation inducing apoptosis include Fas/Apo-1/CD95 ligand, Fas antibody, TNF (tumor necrosis factor) and the like [Cell, 88, 355–365 (1997)]. As compounds suppressing apoptosis, various peptide caspase inhibitors as cysteine protease inhibitors and the like are known; however, the compounds have problems in instability inherent to peptide compounds and insufficient potency.

Antitumor agents clinically used at present can achieve temporal retraction or disappearance of cancers on the basis of their cytotoxicity. However, as they act on healthy cells to cause serious adverse effects, their applications are much limited. In addition, among gastric cancers, colon cancers, pancreatic cancers and the like, there are a number of naturally resistant cancers to which anticancer agents are almost ineffective, or appearance of acquired resistant cancer cells to which primarily effective anticancer agents become ineffective, which causes a serious problem.

Recently, so-called tumor angiogenesis for supplying nutriment and oxygen to cancer cells has been focused as a mechanism of solid cancer proliferation beyond a certain size. An idea of "a therapy by inhibition of tumor angiogenesis" has been being established in which cancer proliferation is suppressed by inhibiting tumor angiogenesis [European Journal of Cancer, 32A, 2534–2539 (1996)]. Although a number of compounds have already been practically developed as antitumor agents, clinical uses of an angiogenesis inhibitors as early as possible have been desired, because they have advantages that conventional antitumor agents do not have. Some angiogenesis inhibitors have been developed and studied so far; however, novel compounds as potential lead compounds have always been desired strongly.

A recruit mechanism of vascular endothelial cells into a cancer tissue has a number of similarities to a recruit mechanism of leukocytes and the like into inflammatory sites, and therefore, medicaments inhibiting chemotaxis of vascular endothelial cells are expected to have potentials as anti-inflammatory agents as well as angiogenesis inhibitors [Immunity, 12, 121–127 (2000)].

DISCLOSURE OF THE INVENTION

An object of the present invention is to provide novel compounds which are useful as active ingredients of medicaments. More specifically, the object of the present invention is to provide compounds which exert antitumor effect by inhibiting angiogenesis or cell cycle. An another object of the present invention is to provide compounds which have apoptosis suppressive action and are useful for preventive and/or therapeutic treatment of diseases including articular rheumatism, hepatitis with viral infection such as hepatitis B and C and the like.

The inventors of the present invention conducted various studies to achieve the foregoing objects. As a result, they found that novel compounds contained in a culture of a newly collected microorganism, strain BAUA3564, have angiogenesis suppressive activity, apoptosis suppressive activity and cell cycle inhibitory activity and are useful as active ingredients of medicaments. The present invention was achieved on the basis of the above findings.

The present invention thus provides a compound represented by the general formula (I):

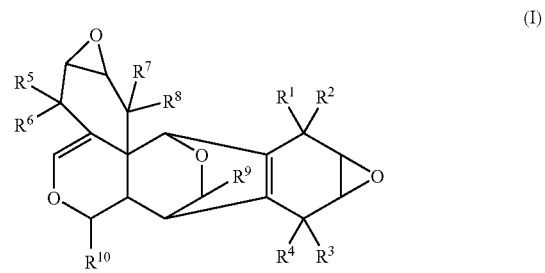

wherein $R^1$ represents hydrogen atom and $R^2$ represents hydroxyl group, or $R^1$ and $R^2$ may combine together to represent oxo group or oxime group; $R^3$ represents hydrogen atom and $R^4$ represents hydroxyl group, or $R^3$ and $R^4$ may combine together to represent oxo group or oxime group; $R^5$ represents hydrogen atom and $R^6$ represents hydroxyl group, or $R^5$ and $R^6$ may combine together to represent oxo group or oxime group; $R^7$ represents hydrogen atom and $R^8$ represents hydrogen atom, or $R^7$ and $R^8$ may combine together to represent oxo group or oxime group; and $R^9$ and $R^{10}$ independently represent hydrogen atom, an optionally substituted alkyl group, or an optionally substituted alkenyl group.

As preferred embodiments of the compound represented by the foregoing general formula (I), provided are a compound wherein $R^1$ is hydrogen atom, $R^2$ is hydroxyl group, $R^3$ and $R^4$ combine together to represent oxo group, $R^5$ is hydrogen atom, $R^6$ is hydroxyl group, $R^7$ and $R^8$ combine together to represent oxo group, and $R^9$ and $R^{10}$ are both methyl groups, and a compound wherein $R^1$ and $R^2$ combine together to represent oxo group, $R^3$ and $R^4$ combine together to represent oxo group, $R^5$ and $R^6$ combine together to represent oxo group, $R^7$ and $R^8$ combine together to represent oxo group, and $R^9$ and $R^{10}$ are both methyl groups.

According to another aspect of the present invention, provided is a compound represented by the general formula (II):

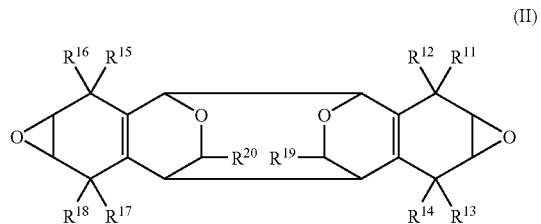

wherein $R^{11}$ represents hydrogen atom and $R^{12}$ represents hydroxyl group, or $R^{11}$ and $R^{12}$ may combine together to represent oxo group or oxime group; $R^{13}$ represents hydrogen atom and $R^{14}$ represents hydroxyl group, or $R^{13}$ and $R^{14}$ may combine together to represent oxo group or oxime group; $R^{15}$ represents hydrogen atom and $R^{16}$ represents hydroxyl group, or $R^{15}$ and $R^{16}$ may combine together to represent oxo group or oxime group; $R^{17}$ represents hydrogen atom and $R^{18}$ represents hydrogen atom, or $R^{17}$ and $R^{18}$ may combine together to represent oxo group or oxime group; and $R^{19}$ and $R^{20}$ independently represent hydrogen atom, an optionally substituted alkyl group, or an optionally substituted alkenyl group.

As a preferred embodiment of the compound represented by the foregoing general formula (II), the present invention provides a compound wherein $R^{11}$ is hydrogen atom, $R^{12}$ is hydroxyl group, $R^{13}$ and $R^{14}$ combine together to represent oxo group, $R^{15}$ is hydrogen atom, $R^{16}$ is hydroxyl group, $R^{17}$ and $R^{18}$ combine together to represent oxo group, and $R^{19}$ and $R^{20}$ are both methyl groups.

From a further aspect of the present invention, provided is a medicament which comprises the compound represented by the foregoing general formula (I) or (II) as an active ingredient. The medicament is useful as an angiogenesis inhibitor, an apoptosis suppressant, or a cell cycle inhibitor, and can be used as an antitumor agent, or a medicament for preventive and/or therapeutic treatment of a disease in which abnormal acceleration of apoptosis is involved. More specifically, the medicament of the present invention is useful, for example, as an antitumor agent as well as a medicament for preventive and/or therapeutic treatment of articular rheumatism, hepatitis with viral infection such as hepatitis B and C, fulminant hepatitis, diabetes and its complications, myocardial infarction, ulcerative colitis, brightism, alopecia, neurodegenerative diseases such as Alzheimer's disease and Parkinson's disease, ischemic brain damage, acquired immune deficiency syndrome, ecstatic cardiomyopathy and the like.

From further aspects of the present invention, provided are an use of the compound represented by the foregoing general formula (I) or (II) for manufacture of the foregoing medicament; a method for inhibition of angiogenesis which comprises the step of administering a therapeutically effective amount of the compound represented by the foregoing general formula (I) or (II) to a mammal including a human; a method for control of apoptosis, preferably, a method for suppression of apoptosis, which comprises the step of administering a therapeutically effective amount of the compound represented by the foregoing general formula (I) or (II) to a mammal including a human; and a method for therapeutic treatment of malignant tumors which comprises the step of administering a therapeutically effective amount of the compound represented by the foregoing general formula (I) or (II) to a mammal including a human.

The present invention also provides a method for preventive and/or therapeutic treatment of a disease in which abnormal acceleration of apoptosis is involved which comprises the step of administering a therapeutically effective amount of the compound represented by the foregoing general formula (I) or (II) to a mammal including a human; a method for therapeutic treatment of excess inflammation which comprises the step of administering a therapeutically effective amount of the compound represented by the foregoing general formula (I) or (II) to a mammal including a human; a method for control of chemotaxis of vascular endothelial cells which comprises the step of administering a therapeutically effective amount of the compound represented by the foregoing general formula (I) or (II) to a mammal including a human; and a method for control of progress of the cell cycle which comprises the step of contacting an effective amount of the compound represented by the foregoing general formula (I) or (II) to cells.

BEST MODE FOR CARRYING OUT THE INVENTION

The alkyl group represented by $R^9$, $R^{10}$, $R^{19}$, or $R^{20}$ may be a straight or branched chain alkyl group, a cyclic alkyl group, or a combination thereof. As the alkyl group, for example, an alkyl group having 1 to 6 carbon atoms, preferably a straight or branched chain alkyl group having 1 to 6 carbon atoms, can be used. More specifically, methyl group, ethyl group, n-propyl group, isopropyl group, n-butyl group, isobutyl group, sec-butyl group, tert-butyl group, n-pentyl group, n-hexyl group and the like can be used. The alkyl group represented by $R^9$, $R^{10}$, $R^{19}$, or $R^{20}$ may be substituted. The number, sort and position of the substituent are not particularly limited. The examples include a halogen atom, amino group, hydroxyl group, carboxyl group, oxo group and the like.

The alkenyl group represented by $R^9$, $R^{10}$, $R^{19}$, or $R^{20}$ is preferably a group containing one or more double bonds in the alkyl group explained above. The alkenyl group represented by $R^9$, $R^{10}$, $R^{19}$, or $R^{20}$ may be substituted. The number, sort and position of the substituent are not particularly limited. The examples include a halogen atom, amino group, hydroxyl group, carboxyl group, oxo group and the like. As $R^9$, $R^{10}$, $R^{19}$, or $R^{20}$, methyl group is preferred.

The compound represented by the general formula (I) or (II) according to the present invention has plural asymmetric carbon atoms, and may sometimes have another or more asymmetric carbon atoms depending on the sort of substituents. Stereoisomers such as optical isomers and diastereomers based on the asymmetric carbon atoms exist. The stereoisomers in a pure form as well as mixtures of any stereoisomers or racemates fall within the scope of the present invention. When the compound of the present invention has an olefinic double bond, geometrical isomers based on the double bond exist, and the geometrical isomers in a pure form as well as mixtures of any geometric isomers fall within the scope of the present invention. In addition, there is a possibility that the compound of the present invention may exist as tautomers, and any tautomers and mixtures thereof also fall within the scope of the present invention. The compound of the present invention can exist as crystals in any forms, or may sometimes exist as a hydrate or solvate. All of these substances naturally fall within the scope or the present invention.

In the specification, among the compounds represented by the general formula (I), two isomers of the compound wherein $R^1$ is hydrogen atom, $R^2$ is hydroxyl group, $R^3$ and $R^4$ combine together to represent oxo group, $R^5$ is hydrogen atom, $R^6$ is hydroxyl group, $R^7$ and $R^8$ combine together to represent oxo group, and $R^9$ and $R^{10}$ are both methyl groups may sometimes be referred to as "RKB-3564A" and "RKB-3564B," and two isomers of the compound wherein $R^1$ and $R^2$ combine together to represent oxo group, $R^3$ and $R^4$ combine together to represent oxo group, $R^5$ and $R^6$ combine together to represent oxo group, $R^7$ and $R^8$ combine together to represent oxo group, and $R^9$ and $R^{10}$ are both methyl groups may sometimes be referred to as "RKB-3564E" and "RKB-3564F". Among the compounds represented by the general formula (II), the compound wherein $R^{11}$ is hydrogen atom, $R^{12}$ is hydroxyl group, $R^{13}$ and $R^{14}$ combine together to represent oxo group, $R^{15}$ is hydrogen atom, $R^{16}$ is hydroxyl group, $R^{17}$ and $R^{18}$ combine together to represent oxo group, and $R^{19}$ and $R^{20}$ are both methyl groups may sometimes be referred to as "RKB-3564D".

The compound represented by the general formula (I) or (II) according to the present invention can be separated and collected from a culture of a microorganism, or prepared by a method of chemical modification of the compound of the present invention which is separated and collected from a culture of a microorganism as a starting material. An example of the microorganism that can produce the compound of the present invention includes strain BAUA-3564 belonging to Oidiomycetes. The microorganism is cultured in a medium composition under a culture condition which are ordinarily used, and then RKB-3564A, RKB-3564B, RKB-3564D, RKB-3564E, and RKB-3564F contained in the culture can be separated and collected. Strain BAUA-3564 has been deposited as international deposition under Budapest Treaty in Patent and Bio-Resource Center of National Institute of Advanced Industrial Science and Technology (Chuo-6, 1-1-1, Higashi, Tsukuba, Ibaraki, Japan) with the accession number of FERM BP-8001 on Apr. 5, 2002 (said deposition has been transferred from the deposition under accession number of FERM P-18284 deposited in the aforementioned authority on Apr. 2, 2001).

As a medium for preparing the compound of the present invention, any of synthetic mediums or natural mediums can be suitably used so long as they appropriately contain a carbon source, a nitrogen source, and inorganic salts. If necessary, mediums may be added with vitamins and other nutrient substances.

As the carbon source, one or more kinds of sources may suitably be chosen and used in consideration of auxotrophy of a microorganism from general carbon sources, for example, sugars such as glucose, maltose, fructose, sucrose, and starch, alcohols such as glycerol, and mannitol, amino acids such as glycine, alanine, and asparagine, and oils and fats such as soy bean oil and olive oil. Examples of the nitrogen source include organic nitrogen-containing compounds such as soy bean powder, corn steep liquor, beef extract, peptone, yeast extract, amino acid mixtures, and fish powder, and inorganic nitrogen compounds such as ammonium salts and nitrates, and one or more kinds of the sources may suitably be chosen and used in consideration of auxotrophy of a microorganism. As the inorganic salt, for example, calcium carbonate, sodium chloride, potassium chloride, magnesium sulfate, cupper sulfate, manganese chloride, zinc sulfate, cobalt chloride, and various phosphates may be added, if necessary. A defoaming agent such as vegetable fats and polypropylene alcohols can also be added, if necessary.

A cultivation temperature may appropriately be chosen and changed within a range that allows growth of a microorganism and effective production of the compound of the present invention. Preferred cultivation temperature is from 10° C. to 32° C., and more preferably from 20° C. to 25° C. pH at the beginning of the cultivation is preferably from about 6 to 8, and cultivation period of time is generally about one day to a few weeks. In general, the cultivation may be terminated when a produced amount of the compound of the present invention reaches to an amount suitable for collection, preferably reaches to the maximum amount. As a cultivation method, any method ordinarily used can be suitably employed such as solid layer cultivation and normal stirring cultivation.

In order to separate and collect the compound of the present invention from the culture liquid after the cultivation, any means ordinarily used for generally collecting microbial metabolites can be appropriately applied. Examples include separation methods using various ion exchange resins, nonionic adsorbing resins or other, separation methods using chromatography such as gel filtration chromatography, chromatography with adsorbent such as activated charcoal, alumina, and silica gel, or high performance liquid chromatography, or crystallization, concentration under reduced pressure, or lyophilization, which means can be used alone or in appropriate combination thereof, or repeatedly.

The compound of the present invention that is separated and collected from the culture liquid is further chemically modified, and thereby the other compounds of the present invention can be prepared. For example, a compound having oxime group can be prepared by using a compound having oxo group through ordinary chemical modification. Conversion of the functional group from oxo group to oxime group can easily be made according to the conventional method that is well known in the art, for example, by reacting with hydroxylamine in an inert organic solvent at room temperature or under heating.

The compound of the present invention has angiogenesis suppressive activity, apoptosis suppressive activity, and cell cycle inhibitory activity as shown in the test examples mentioned below, and is useful as an antitumor agent as well as a medicament for preventive and/or therapeutic treatment of a disease in which abnormal acceleration of apoptosis is involved, or a medicament for preventive and/or therapeutic treatment of a disease in which excess angiogenesis is involved. Examples of diseases in which cell death is accelerated due to a deviation from a normal apoptosis control mechanism include, for example, articular rheumatism, hepatitis with viral infection such as hepatitis B and C, fulminant hepatitis, diabetes, myocardial infarction, ulcerative colitis, brightism, alopecia, neurodegenerative diseases such as Alzheimer's disease and Parkinson's disease, ischemic brain damage, acquired immune deficiency syndrome, ecstatic cardiomyopathy and the like. Examples of diseases in which excess angiogenesis is involved include malignant tumors as well as diabetic vascular complications (e.g., diabetic retinopathy) and the like.

A route of administration, a dosage form, and a dose of the medicament of the present invention can be appropriately chosen depending on a purpose of administration. The route of administration of the medicament of the present invention may be oral administration or parenteral administration. The form of the medicament of the present invention is not particularly limited, and examples include oral preparations such as tablets, powders, capsules, granules, extracts, and syrups, and parenteral preparations such as injections, drip infusions, and suppositories. These preparations can be manufactured as pharmaceutical compositions according to known methods by using pharmaceutically acceptable additives such as excipients and binders. A dose of the medicament comprising the compound of the present invention as an active ingredient may usually be from 0.1 mg to 100 mg/kg, preferably from 1 mg to 20 mg/kg, per day for oral administration for an adult, and from 0.01 mg to 10 mg/kg, preferably from about 0.1 to 2 mg/kg, per day for parenteral administration for an adult, which may be increased or decreased depending on the age and body weight of a patient, sensitivity, a degree of symptom and the like. The aforementioned dose can be administered once a day or several times a day as divided portions. However, a dose beyond the aforementioned range can be administered, if necessary.

The use of the compound represented by the aforementioned general formula (I) or (II) according to the present invention is not limited to the aforementioned use as a medicament. For example, when the compound of the present invention is used as a reagent, the compound can be used by dissolving said compound in an organic solvent or a water-containing organic solvent. For example, cell growth can be inhibited by direct application to various culture cell systems. Examples of usable organic solvent include methanol, ethanol, dimethyl sulfoxide and the like. The reagent form is not particularly limited, and examples include solid preparations such as powders, or liquid preparations dissolved in an organic solvent or a water-containing organic solvent. When the aforementioned compound is used as a reagent for exerting cell growth inhibitory action, an effective amount is from 0.1 to 100 μg/ml. An appropriate amount may differ depending on a type of a culture cell system and a purpose of using the reagent, which can suitably be chosen by a person with ordinary skill in the art. The amount out of the aforementioned range can be applied, if necessary.

EXAMPLES

Example 1

Strain BAUA-3564 (FERM P-18284) was inoculated into a medium comprising glucose 1.0%, soluble starch 2.0%, soy bean powder 1.5%, malt extract 0.5%, vegetable extract 10%, potassium diphosphate 0.05%, potato dextrose 2.6%, and magnesium sulfate 0.05%, and then cultivation was carried out with shaking at 28° C. for 72 hours. The culture (210 ml) was inoculated to a medium of the same composition (15 liters), and cultivation was carried out with shaking at 28° C. for 96 hours.

The aforementioned culture was separated into bacterial mass and a supernatant by using a centrifugal separator, and the supernatant was adjusted to pH 7.0 and extracted with 15 liters of ethyl acetate. After extraction, all ethyl acetate layers were combined and concentrated under reduced pressure to give brown syrup 5.0 g. The syrup was dissolved in chloroform (10 ml) and applied to a silica gel column charged with chloroform (4 cm diameter, 60 cm length). Initially, elution was performed with chloroform (600 ml), then with each 600 ml of a chloroform/methanol solution having a successively changed mixing ratio (100:1, 50:1, 20:1, 10:1, 5:1, 1:1).

The compound of the present invention, RKB-3564A, was eluted in a fraction with the chloroform/methanol solution (20:1). The fraction was concentrated under reduced pressure to give brown syrup 2.5 g. Then, the brown syrup 2.5 g was dissolved in methanol 25 ml and made into aliquots, and purified by high performance liquid chromatography (acetonitrile:water=2:8→acetonitrile:water=4:6; linear gradient, flow rate 9.0 ml/min) using a reverse phase ODS column (2 cm diameter, 25 cm length, PEGASIL ODS, Senshu Kagaku Co.) to give RKB-3564A. Recrystallization was further carried out from a mixed solvent of ethyl acetate/dichloromethane/methanol to give pure RKB-3564A (60 mg) as colorless needles.

The compound of the present invention, RKB-3564B, was eluted in a fraction with the chloroform/methanol solution (10:1). The fraction was concentrated under reduced pressure to give brown syrup 1.1 g. Then, the brown syrup 1.1 g was dissolved in methanol 1.1 ml and made into aliquots, and purified by high performance liquid chromatography (acetonitrile:water=2:8→acetonitrile:water=5:5; linear gradient, flow rate 9.0 ml/min) using a reverse phase ODS column (2 cm diameter, 25 cm length, PEGASIL ODS, Senshu Kagaku Co.) to give RKB-3564B. Thin layer silica gel column chromatography (chloroform:methanol=10:1) was further carried out to give RKB-3564B (50 mg) as colorless oil.

The fraction eluted with the chloroform/methanol solution (50:1) was purified by high performance liquid chromatography (acetonitrile:water=3:7 →acetonitrile:water=5:5; linear gradient, flow rate 9.0 ml/min) using a reverse phase ODS column (2 cm diameter, 25 cm length, PEGASIL ODS, Senshu Kagaku Co.) to give RKB-3564D. Thin layer silica gel column chromatography (chloroform:methanol=30:1) was further carried out to give RKB-3564D (9 mg) as colorless oil. RKB-3564E and RKB-3564F can be isolated from the culture product by the same purification process, and the compounds can also be prepared from RKB-3564A and RKB-3564B, respectively, by oxidizing hydroxyl groups at the 3-position and the 3'-position in a conventional method, for example, oxidation with Dess-Martin periodinate.

RKB-3564A

NMR data are shown in Table 1 (solvent: deuterated acetone, δ ppm, internal standard: TMS, $^{13}$C: 125 MHz, $^1$H: 500 MHz).

Appearance: colorless needles

Specific rotation: +61.0 (c=0.146, 21° C., methanol)

Melting point: 186° C. (dec.)

Molecular formula: $C_{20}H_{20}O_8$

High-resolution mass spectrum (HR-EIMS): (M+)

Found (m/z): 388.1148

Calcd. (m/z): 388.1158

UV λ max nm (methanol) (ε): 205 (10540), 265 (sh, 3565), 320 (930)

IR ν max (KBr) cm$^{-1}$: 3350, 1705, 1675, 1370, 1280, 1050, 1685

$R_f$ value (Silica gel 60 $F_{254}$, Merck)

0.48 (solvent; $CHCl_3$:methanol=10:1)

Color reaction (positive): 10% sulfuric acid

Solubility: easily soluble in methanol or dimethyl sulfoxide. Insoluble in n-hexane.

TABLE 1

| position | 13C (multiplicity) | 1H (multiplicity) | (J/Hz) |
|---|---|---|---|
| 1 | 72.39 d | 5.23 s | |
| 2 | 153.52 s | | |
| 3 | 63.91 d | 4.69 br s | |
| 4 | 58.76 d | 3.74 d | 3.7 |
| 5 | 53.61 d | 3.44 d | 3.7 |
| 6 | 190.18 s | | |
| 7 | 134.36 s | | |
| 8 | 39.29 d | 3.11 br s | |
| 9 | 66.99 d | 4.29 dq | 2.6, 6.3 |
| 10 | 20.93 q | 0.71 d | 6.3 |
| 1' | 142.42 d | 6.73 s | |
| 2' | 115.05 s | | |
| 3' | 64.15 d | 4.94 d | 6.8 |
| 4' | 66.65 d | 3.76 d | 3.7 |
| 5' | 56.34 d | 3.40 d | 3.7 |
| 6' | 200.72 s | | |
| 7' | 50.66 s | | |
| 8' | 38.02 d | 2.44 s | |
| 9' | 74.78 d | 4.43 q | 6.3 |
| 10' | 20.27 q | 1.00 d | 6.3 |
| 3-OH | | 4.69 br s | |
| 3'-OH | | 4.97 d | 6.8 |

RKB-3564B

NMR data are shown in Table 2 (solvent: deuterated chloroform, δ ppm, internal standard: TMS, $^{13}$C: 125 MHz, $^1$H: 500 MHz).

Appearance: colorless oil

Specific rotation: +153.0 (c=0.315, 21° C., methanol)

Molecular formula: $C_{20}H_{20}O_8$

High-resolution mass spectrum (HR-EIMS): (M+)

Found (m/z): 388.1135

Calcd. (m/z): 388.1158

UV λ max nm (methanol) (ε): 205 (13140), 240 (5970), 320 (430)

IR ν max (neat) cm$^{-1}$: 3425, 1685, 1675, 1340, 1190, 1000

$R_f$ value (Silica gel 60 $F_{254}$, Merck)

0.58 (solvent; CHCl$_3$:methanol=10:1)

Color reaction (positive): 10% sulfuric acid

Solubility: easily soluble in methanol or dimethyl sulfoxide. Insoluble in n-hexane.

TABLE 2

| position | 13C (multiplicity) | 1H (multiplicity) | (J/Hz) |
|---|---|---|---|
| 1 | 73.15 d | 5.06 s | |
| 2 | 150.03 s | | |
| 3 | 63.76 d | 4.84 br s | |
| 4 | 56.17 d | 3.82 dd | 1.3, 3.4 |
| 5 | 52.53 d | 3.55 d | 3.4 |
| 6 | 190.80 s | | |
| 7 | 132.86 s | | |
| 8 | 36.76 d | 3.11 dd | 1.0, 2.6 |
| 9 | 70.47 d | 4.16 dq | 2.6, 6.3 |
| 10 | 20.02 q | 0.80 d | 6.3 |
| 1' | 149.87 d | 6.50 s | |
| 2' | 105.72 s | | |
| 3' | 68.36 d | 4.65 br s | |
| 4' | 54.59 d | 3.63 dd | 2.1, 3.1 |
| 5' | 52.49 d | 3.52 d | 3.1 |
| 6' | 198.85 s | | |
| 7' | 51.59 s | | |
| 8' | 41.83 d | 2.78 dd | 2.1, 6.3 |
| 9' | 74.42 d | 3.54 q | 6.3 |
| 10' | 19.37 q | 1.28 d | 6.3 |
| 3-OH | | 4.37 br s | |
| 3'-OH | | 3.98 br s | |

RKB-3564D

NMR data are shown in Table 3 (solvent: deuterated acetone, δ ppm, internal standard: TMS, $^{13}$C: 125 MHz, $^1$H: 500 MHz).

Appearance: colorless oil

Specific rotation: +303.3 (c=0.184, 21° C., acetone)

Molecular formula: $C_{20}H_{20}O_8$

High-resolution mass spectrum (HR-EIMS): (M+)

Found (m/z): 388.1173

Calcd. (m/z): 388.1158

UV λ max nm (methanol) (ε): 238 (7490), 255 (sh, 6590)

IR ν max (neat) cm$^{-1}$: 3450, 1670, 1620, 1255

$R_f$ value (Silica gel 60 $F_{254}$, Merck): 0.67 (solvent; CHCl$_3$:methanol=10:1)

Color reaction (positive): 10% sulfuric acid

Solubility: easily soluble in methanol or dimethyl sulfoxide. Insoluble in n-hexane.

TABLE 3

| position | 13C (multiplicity) | 1H (multiplicity) | (J/Hz) |
|---|---|---|---|
| 1, 1' | 81.57 d | 4.79 br s | |
| 2, 2' | 155.58 s | | |

TABLE 3-continued

| position | $^{13}C$ (multiplicity) | $^1H$ (multiplicity) | (J/Hz) |
|---|---|---|---|
| 3, 3' | 66.19 d | 4.60 d | 7.8 |
| 4, 4' | 58.45 d | 3.85 dd | 0.9, 3.7 |
| 5, 5' | 53.45 d | 3.52 dd | 0.9, 3.7 |
| 6, 6' | 192.65 s | | |
| 7, 7' | 132.67 s | | |
| 8, 8' | 39.92 d | 3.21 br s | |
| 9, 9' | 72.82 d | 4.19 d | 6.4 |
| 10, 10' | 23.01 q | 0.76 d | 6.4 |
| 3-OH, 3'-OH | | 4.37 br d | 8.2 |

RKB-3564E, RKB-3564F

Both compounds can be colored by heating after spraying with 10% sulfuric acid, and are easily soluble in methanol or dimethyl sulfoxide and insoluble in n-hexane.

| | RKB-3564E | RKB-3564F |
|---|---|---|
| Appearance | Colorless | Colorless |
| Molecular formula | $C_{20}H_{16}O_8$ | $C_{20}H_{16}O_8$ |
| EI-MS (m/z) | 384 | 384 |

Test Example 1

Inhibition of Chemotaxis of Vascular Endothelial Cells by RKB-3564A, RKB-3564B, RKB-3564D, RKB-3564E, and RKB-3564F HUVEC cells, normal human unbilical vein vascular endothelial cells maintained in HuMedia-EG2 (KURABO) medium, were inoculated on the upper layer of a three-dimensional culture using a chemotaxel chamber. HuMedia-EG2 containing vascular endothelial cell growth factor (VEGF) was charged in the lower layer to induce chemotaxis of HUVEC cells. RKB-3564A, RKB-3564B, RKB-3564D, RKB-3564E, and RKB-3564F each inhibited chemotaxis of HUVEC cells induced by VEGF in the concentration of from 0.1 to 1 µg/ml. These results indicate that the aforementioned compounds of the present invention have anti-VEGF action and are effective as medicaments such as angiogenesis inhibitors, antitumor agents, and anti-inflammatory agents.

Test Example 2

Suppressive Activity of Fas Antibody-induced Apoptosis by RKB-3564A, RKB-3564B, RKB-3564D, RKB-3564E, and RKB-3564F Jurkat cells, an adult T cell leukemia cell line expressing Fas, were used as Fas antibody sensitive cells. The Jurkat cells were cultured in a RPMI medium containing 10% calf serum in an incubator that contained 5% carbon dioxide and was saturated with stream. The Jurkat cells in the logarithmic proliferation period were added with RKB-3564A, RKB-3564B, RKB-3564D, RKB-3564E, and RKB-3564F in a series of dilution, and cultured in the presence of Fas antibody, CH-11 (Medical & Biological Laboratories Co., Ltd., 100 ng/ml) for 6 hours, and the survival rate of the cells was assayed by the MTT method. The survival rate was calculated according to the following formula.

Survival rate (%)={[(absorbance in the presence of anti-Fas antibody and the compound)−(absorbance in the presence of anti-Fas antibody and in the absence of the compound)]/[(absorbance in the absence of anti-Fas antibody and the compound)−(absorbance in the presence of anti-Fas antibody and in the absence of the compound)]}×100

The concentration that inhibited 50% of apoptosis, which was induced by Fas antibody, was about 3 to 10 µg/ml for each of RKB-3564A, RKB-3564B, RKB-3564D, RKB-3564E, and RKB-3564F. These results indicate that the aforementioned compounds of the present invention have anti-apoptosis action and are effective as medicaments for preventive and/or therapeutic treatment of inflammatory diseases in which abnormal acceleration of apoptosis is involved.

Test Example 3

Cell Cycle Inhibitory Activity of RKB-3564A, RKB-3564B, RKB-3564D, RKB-3564E, and RKB-3564F Cell cycle inhibitory activity of RKB-3564A, RKB-3564B, RKB-3564D, RKB-3564E, and RKB-3564F were measured in H1299 cells, human lung carcinoma cells in which p53 as a tumor suppressor gene was deleted. The H1299 cells were cultured in a DMEM medium (Dulbecco's modified Eagle medium) containing 10% calf serum in an incubator that contained 5% carbon dioxide and was saturated with stream. The H1299 cells in the logarithmic proliferation period were added with RKB-3564A, RKB-3564B, RKB-3564D, RKB-3564E, and RKB-3564F in a series of dilution, and the progress of the cell cycle of the H1299 cells was analyzed by a flow cytometer after 24 hours. The compounds of the present invention each terminated the cell cycle in the G1 period in the concentration of about 0.3 to 3 µg/ml. These results indicate that the aforementioned compounds of the present invention have action of inhibiting the cell cycle and are effective as antitumor agents.

Preparation Example 1

Injection and Drip Infusion

RKB-3564A, RKB-3564B, RKB-3564D, RKB-3564E, or RKB-3564F is aseptically divided and sealed in vials so as to contain 10 mg of the compound with powder glucose (5 g), and the vials are charged with an inert gas such as nitrogen or helium and stored in a cool and dark place. The preparation is dissolved in ethanol and added with 0.85% physiological saline (100 ml) before use to prepare an intravenous injection and administered by intravenous injection or drip infusion in the amount of from 10 to 100 ml per day depending on symptoms.

Preparation Example 2

Granules

RKB-3564A, RKB-3564B, RKB-3564D, RKB-3564E, or RKB-3564F (1 g), lactose (98 g), and hydroxypropyl cellulose (1 g) are well mixed, and then formed into particles according to a conventional method. The resulting particles were well dried to prepare granules suitable for a package in a bottle or a heat seal container. The granules can be orally administered in a dose of from 100 to 1,000 mg per day depending on symptoms.

INDUSTRIAL APPLICABILITY

The compound of the present invention has angiogenesis suppressive activity, apoptosis suppressive activity and cell cycle inhibitory activity, and is useful as an active ingredient of an antitumor agent or a medicament for preventive and/or therapeutic treatment of a disease in which abnormal acceleration of apoptosis is involved.

What is claimed is:

1. A compound represented by the general formula (I):

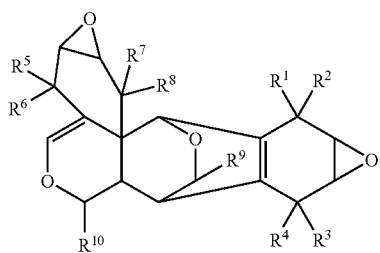

(I)

wherein $R^1$ represents hydrogen atom and $R^2$ represents hydroxyl group, or $R^1$ and $R^2$ may combine together to represent oxo group or oxime group; $R^3$ represents hydrogen atom and $R^4$ represents hydroxyl group, or $R^3$ and $R^4$ may combine together to represent oxo group or oxime group; $R^5$ represents hydrogen atom and $R^6$ represents hydroxyl group, or $R^5$ and $R^6$ may combine together to represent oxo group or oxime group; $R^7$ represents hydrogen atom and $R^8$ represents hydrogen atom, or $R^7$ and $R^8$ may combine together to represent oxo group or oxime group; and $R^9$ and $R^{10}$ independently represent hydrogen atom, an optionally substituted alkyl group, or an optionally substituted alkenyl group.

2. The compound according to claim 1, wherein $R^1$ is hydrogen atom, $R^2$ is hydroxyl group, $R^3$ and $R^4$ combine together to represent oxo group, $R^5$ is hydrogen atom, $R^6$ is hydroxyl group, $R^7$ and $R^8$ combine together to represent oxo group, and $R^9$ and $R^{10}$ are both methyl groups.

3. The compound according to claim 1, wherein $R^1$ and $R^2$ combine together to represent oxo group, $R^3$ and $R^4$ combine together to represent oxo group, $R^5$ and $R^6$ combine together to represent oxo group, $R^7$ and $R^8$ combine together to represent oxo group, and $R^9$ and $R^{10}$ are both methyl groups.

4. A compound represented by the general formula (II):

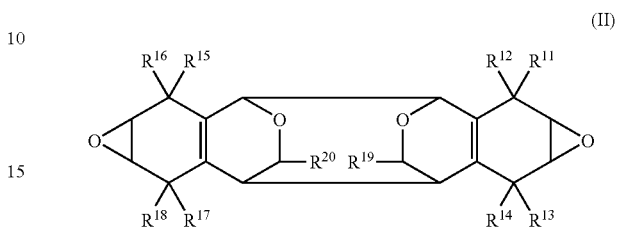

(II)

wherein $R^{11}$ represents hydrogen atom and $R^{12}$ represents hydroxyl group, or $R^{11}$ and $R^{12}$ may combine together to represent oxo group or oxime group; $R^{13}$ represents hydrogen atom and $R^{14}$ represents hydroxyl group, or $R^{13}$ and $R^{14}$ may combine together to represent oxo group or oxime group; $R^{15}$ represents hydrogen atom and $R^{16}$ represents hydroxyl group, or $R^{15}$ and $R^{16}$ may combine together to represent oxo group or oxime group; $R^{17}$ represents hydrogen atom and $R^{18}$ represents hydrogen atom, or $R^{17}$ and $R^{18}$ may combine together to represent oxo group or oxime group; and $R^{19}$ and $R^{20}$ independently represent hydrogen atom, an optionally substituted alkyl group, or an optionally substituted alkenyl group.

5. The compound according to claim 4, wherein $R^{11}$ is hydrogen atom, $R^{12}$ is hydroxyl group, $R^{13}$ and $R^{14}$ combine together to represent oxo group, $R^{15}$ is hydrogen atom, $R^{16}$ is hydroxyl group, $R^{17}$ and $R^{18}$ combine together to represent oxo group, and $R^{19}$ and $R^{20}$ are both methyl groups.

6. A pharmaceutical composition comprising as an active ingredient an amount of a compound according to any one of claims 1–5 effective to inhibit apoptosis or to inhibit angiogenesis in a subject to whom the composition is administered, and a pharmaceutically acceptable carrier.

7. The pharmaceutical composition of claim 6, in which the active ingredient is formulated so as to provide an oral dosage of from 0.1 mg/kg to 100 mg/kg per day to the subject.

8. The pharmaceutical composition of claim 6, in which the active ingredient is formulated so as to provide a parenteral dosage of from 0.01 mg/kg to 10 mg/kg per day to the subject.

9. A method for treating a disease selected from the group consisting of articular rheumatism, hepatitis B, hepatitis C, fulminant hepatitis, myocardial infarction, lcerative colitis, Alzheimer's disease, Parkinson's disease, ischemic brain damage, acquired immune deficiency syndrome, ecstatic cardiomyopathy malignant tumors, comprising administering the pharmaceutical composition of claim 6 to a subject exhibiting one of said diseases.

* * * * *